United States Patent [19]

Tanaka et al.

[11] Patent Number: 5,087,480
[45] Date of Patent: Feb. 11, 1992

[54] METHOD FOR MANUFACTURING A MOISTURE PERMEABLE ELECTRODE IN A MOISTURE SENSOR

[75] Inventors: Junichi Tanaka, Tenri; Hisatoshi Furubayashi, Yamatokoriyama; Masanori Watanabe, Tenri, all of Japan

[73] Assignee: Sharp Kabushiki Kaisha, Osaka, Japan

[21] Appl. No.: 380,741

[22] Filed: Jul. 17, 1989

Related U.S. Application Data

[63] Continuation of Ser. No. 684,347, Dec. 20, 1984, abandoned.

[30] Foreign Application Priority Data

Dec. 27, 1983 [JP] Japan .................. 58-247175

[51] Int. Cl.$^5$ ............................................ H01G 5/20
[52] U.S. Cl. ..................................... 427/79; 427/124; 427/250; 361/286
[58] Field of Search .................. 427/79, 124, 250; 361/286

[56] References Cited

U.S. PATENT DOCUMENTS

| | | | |
|---|---|---|---|
| 4,437,227 | 3/1984 | Flannery | 427/63 |
| 4,438,480 | 3/1984 | Chambaz | 361/278 |
| 4,486,464 | 12/1984 | Young | 427/63 |
| 4,496,648 | 1/1985 | Young | 427/63 |

OTHER PUBLICATIONS

Powell et al, Vapor Deposition, John Wiley and Sons, N.Y., ©1966, pp. 233-234.

*Primary Examiner*—Richard Bueker
*Attorney, Agent, or Firm*—Birch, Stewart, Kolasch & Birch

[57] ABSTRACT

A moisture sensing element includes a moisture permeable gold electrode film formed on a moisture sensitive polyvinyl alcohol film which is carried by a glass substrate. The moisture permeable gold electrode film is formed by a vacuum evaporation under a nitrogen gas pressure of $1.0 \times 10^{-3}$ Torr through $1.0 \times 10^{-2}$ Torr. The deposition rate is about 0.5 Å/sec., and the moisture permeable gold electrode film has a thickness of 100 Å through 200 Å.

7 Claims, 1 Drawing Sheet

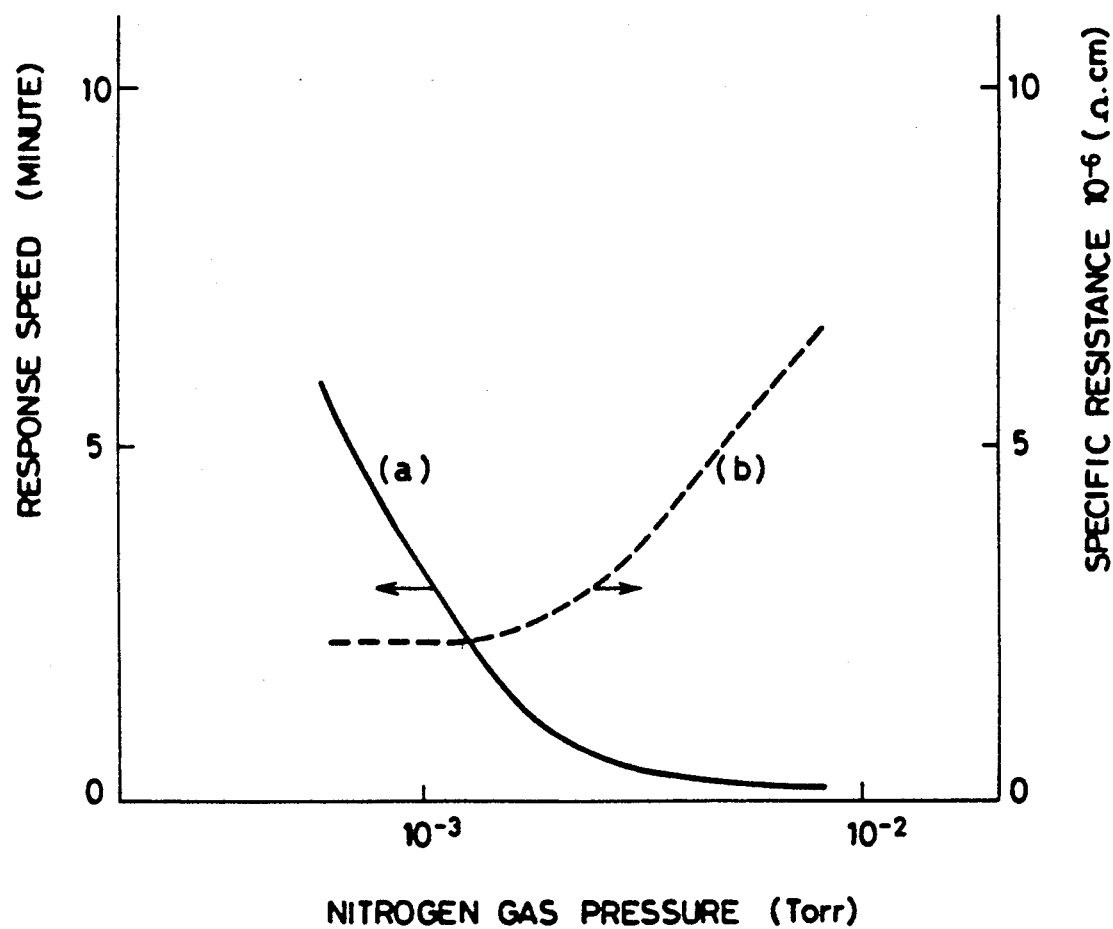

METHOD FOR MANUFACTURING A MOISTURE PERMEABLE ELECTRODE IN A MOISTURE SENSOR

This application is a continuation of application Ser. No. 06/684,347 filed on Dec. 20, 1984, now abandoned.

BACKGROUND OF THE INVENTION

1. Field of the Invention

The present invention relates to a method for manufacturing a moisture permeable electrode for use in a moisture sensing element.

2. Description of the Prior Art

A moisture sensing element has been developed, which includes a moisture sensitive thick-film or a moisture sensitive thin-film made of, for example, a polymer film or a metal oxide film. A pair of electrodes are formed on the opposing major surfaces of the moisture sensitive film so as to detect the impedance representative of the humidity. In such a construction, at least one of the pair of electrodes must be a moisture permeable electrode to ensure the moisture detecting operation.

A gold film is widely used as the electrode in a moisture sensing element. The gold film has a low resistance, and shows a high water resisting property and a high chemical resistance. When the moisture sensing element has a ceramic substrate such as an alumina substrate, the irregularities of the ceramic substrate form irregularities on the surface of the moisture sensitive film without regard to the material of the moisture sensitive film. The thus formed irregular surface provides clearances between the moisture sensitive film and an electrode film formed on the moisture sensitive film, the clearances providing the moisture permeability.

When the moisture sensitive film is made of ceramics such as a metal oxide, the moisture sensitive film itself has an irregular surface. Therefore, a moisture permeable electrode can be formed on the moisture sensitive film. That is, if the moisture sensitive film has an irregular surface, a moisture permeable electrode is formed on the moisture sensitive film. In this case, the material of the electrode film, the thickness of the electrode film, and the deposition condition of the electrode film are not necessarily controlled strictly.

However, if a moisture sensing element has a flat substrate such as a glass substrate, and a flat moisture sensitive film such as a polymer film, preferred moisture permeability is not ensured when the electrode is made of a gold film or a gold alloy film. If the thickness of the electrode film is selected considerably thin, clearances are formed in the electrode film, which provide moisture permeability. However, the specific resistance greatly increases even when the thickness slightly reduces in case the gold electrode film has a thickness less than 100 Å. That is, it is difficult to accurately control the specific resistance of a thin gold film, and the reproducibility of the electrode film is very low.

OBJECTS AND SUMMARY OF THE INVENTION

Objects of the Invention

Accordingly, an object of the present invention is to provide a novel method for manufacturing a moisture permeable gold electrode film in a moisture sensing element.

Another object of the present invention is to form a moisture permeable electrode on a flat moisture sensitive film in a moisture sensing element.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Summary of the Invention

To achieve the above objects, pursuant to an embodiment of the present invention, an electrode film is formed on a moisture sensitive film by a vacuum evaporation method which uses helium gas, neon gas, argon gas, nitrogen gas, oxygen gas, or a mixed gas thereof. The clearances increase, and hence the moisture permeability becomes high as the gas pressure increases. That is, the structure of the electrode film is controlled by the gas pressure in the vacuum evaporation operation. In a preferred form, the gas pressure is selected between $1.0 \times 10^{-3}$ Torr and $1.0 \times 10^{-2}$ Torr. The electrode film shows desirable moisture permeability.

BRIEF DESCRIPTION OF THE DRAWINGS

The present invention will be better understood from the detailed description given hereinbelow and the accompanying drawing which is given by way of illustration only, and thus is not limitative of the present invention and wherein:

The single drawing FIGURE is a graph showing the characteristics of a moisture sensing element when the nitrogen gas pressure for forming a gold electrode film is changed.

DESCRIPTION OF THE PREFERRED EMBODIMENTS

A typical construction of a moisture sensing element is disclosed in copending U.S. Patent Application Ser. No. 590,343, "MOISTURE PERMEABLE ELECTRODE IN A MOISTURE SENSOR", filed on Mar. 16, 1984 by Masanori WATANABE, Hisatoshi FURUBAYASHI, Junichi TANAKA and Masaya HIJIKIGAWA, now U.S. Pat. No. 4,496,931, and assigned to the same assignee as the present application. The British counterpart was filed on Mar. 20, 1984, and was assigned Application No. 8407169. The German counterpart was published on Oct. 4, 1984 as DE-OS 34 10 578. The moisture sensing element of the present invention has the similar construction as that disclosed in the above-mentioned application. The present invention resides in a method for fabricating a moisture permeable electrode in the moisture sensing element. In accordance with the present invention, a moisture sensing element includes a glass substrate, and a moisture sensitive film formed on the glass substrate. The moisture sensitive film is made of a polyvinyl alcohol film which is baked at 250° C. A gold film is formed on the moisture sensitive film by a vacuum evaporation. The evaporation is conducted in a nitrogen gas environment of $6.0 \times 10^{-3}$ Torr through $1.0 \times 10^{-2}$ Torr, and at a deposition rate of 0.5 Å/sec. The substrate is not heated during the deposition, and the gold film is formed to have a thickness of 100 Å.

A curve (a) in the single drawing figure shows a response speed which varies depending on the nitrogen gas pressure under which the gold electrode film is formed on the moisture sensitive film. The response speed is determined by measuring a time period during which the impedance of the moisture sensing element reaches a value which is 90% of a specific impedance corresponding to the relative humidity of 90% when the relative humidity of the environment is changed from 30% to 90%. A curve (b) in the single drawing figure shows a specific resistance of the gold electrode film, which varies depending on the nitrogen gas pressure under which the gold electrode film is formed on the moisture sensitive film. It will be clear from the graph that the clearances in the gold electrode film increase as the nitrogen gas pressure increases. That is, the moisture permeability and the specific resistance increase as the nitrogen gas pressure increases.

If the nitrogen gas pressure is greater than $1 \times 10^{-2}$ Torr, so many clearances are formed in the gold electrode film so many that the electrode film does not have a sufficient strength. Furthermore, when the nitrogen gas pressure is less than $1.0 \times 10^{-3}$ Torr, so few clearances are formed in the gold electrode film that a desired moisture permeability is not obtained. In addition, if the gold electrode film has a thickness greater than 200 Å, a desired moisture permeability is not obtained even when the nitrogen gas pressure is selected at $1 \times 10^{-2}$ Torr. If the gold electrode film has a thickness less than 100 Å, the specific resistance greatly increases when the thickness of the gold electrode film is slightly reduced. That is, the reproducibility of the gold electrode film becomes very low.

Accordingly, the moisture permeable gold electrode film is preferably formed under the nitrogen gas pressure of $1 \times 10^{-3}$ Torr through $1 \times 10^{-2}$ Torr. Furthermore, the moisture permeable gold electrode film preferably has a thickness of 100 Å through 200 Å.

EXAMPLE

A moisture sensitive film is formed on a glass substrate. The moisture sensitive film is made of a polyvinyl alcohol film baked at 250° C. A moisture permeable gold electrode film is formed on the polyvinyl alcohol moisture sensitive film. The evaporation is conducted in a nitrogen gas environment of $9.0 \times 10^{-3}$ Torr. The deposition rate is 0.5 Å/sec., and the substrate is not heated during the deposition. The moisture permeable gold electrode film has a thickness of 125 Å.

The resulting moisture permeable gold electrode film adheres tightly to the moisture sensitive film, and the specific resistance thereof is stable after a storage test under high temperature and high humidity (60° C., 90 to 95%), or even after a water immersion test.

A similar result is obtained when a gold alloy film is employed as the moisture permeable electrode. Further, the evaporation operation is not necessarily conducted in the nitrogen gas environment. Helium gas, neon gas, oxygen gas, argon gas, or a mixed gas thereof can be employed.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A method for manufacturing a moisture sensing element comprising the steps of:
   providing a glass substrate;
   disposing a moisture sensitive polyvinyl alcohol film on said glass substrate, said moisture sensitive polyvinyl alcohol film being composed of a resin and having a flat surface and;
   depositing a moisture permeable gold or gold alloy electrode film having a thickness of 100 Å through 200 Å on said moisture sensitive polyvinyl alcohol film by vacuum evaporation, said vacuum evaporation being carried out under a gas pressure environment of $1.0 \times 10^{-3}$ Torr through $1.0 \times 10^{-2}$ Torr, wherein the gas of said gas pressure environment is helium, neon, argon, nitrogen, oxygen or a mixture thereof,
   wherein said moisture sensing element manufactured has a response speed of not over 3.4 minutes and a specific resistance of not over $7.3 \times 10^{-6}$ ohm.cm, and the specific resistance of the moisture permeable electrode film is stable after storage under high temperature and high humidity conditions.

2. The method of claim 1, wherein said moisture permeable gold or gold alloy electrode film is a gold film having a thickness of about 125 Å.

3. The method of claim 1, wherein said moisture permeable gold or gold alloy electrode film is formed under a nitrogen gas pressure environment of about $9.0 \times 10^{-3}$ Torr, and at a deposition rate of about 0.5 Å/sec.

4. The method of claim 3, wherein said moisture permeable gold or gold alloy electrode film is a gold film.

5. The method of claim 1, wherein said moisture permeable gold or gold alloy electrode film is a gold film.

6. The method of claim 1, wherein said moisture permeable gold or gold alloy electrode film is a gold alloy film.

7. The method of claim 1, wherein the glass substrate is not heated during the depositing of the film.

* * * * *